Dec. 1, 1942. K. A. LUCAL Plant Pat. 557
BUDDLEIA PLANT
Filed Dec. 10, 1941
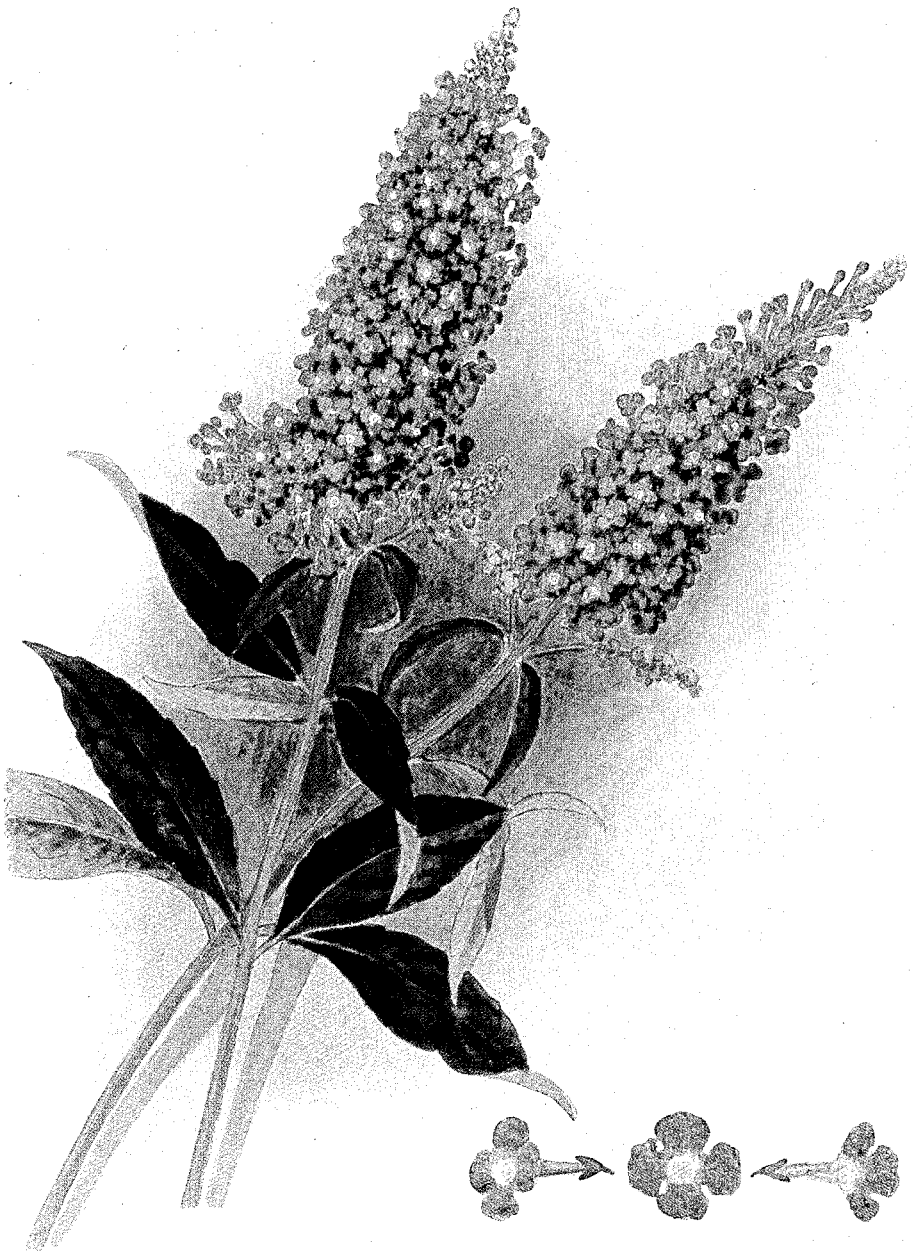
Witness
Addison J. Avery
Inventor
Korle A. Lucal
Rummler Rummler & Davis
Attys.

Patented Dec. 1, 1942

Plant Pat. 557

UNITED STATES PATENT OFFICE

557

BUDDLEIA PLANT

Karle A. Lucal, Springfield, Ohio, assignor to Good & Reese, Inc., Springfield, Ohio, a corporation of Ohio Application December 10, 1941, Serial No. 422,367

1 Claim. (Cl. 47—60)

The new variety of Buddleia plant herein described is a cross between an unnamed seedling and B. Royal Purple, which was made in 1938 at Springfield, Ohio. The novel qualities of this plant have been retained through several generations from cuttings, and have been found to be permanently fixed.

The main object attained in carrying out this invention is the permanent establishing of the peculiar bluish cast in color of this Buddleia, made conspicuous by the contrasting two-toned, orange-colored eye in the center of each floret. Another effect produced is a full and large panicle, more circular in shape than in most Buddleias.

This new variety, in plant structure, is similar to the parent B. Royal Purple. The flower has the usual tubular, four-lobed corolla. The leaves of the plant are short petioled and arranged opposite each other on the stem.

The accompanying illustration shows in full color typical branches of the full-blown blossom, buds; and, at the bottom, from left to right, a floret, in side view, full face view and in section.

The showy panicle of this Buddleia plant presents a strikingly stellate appearance, due to the two-toned eye of each floret and the overtone of bluish color of the whole mass of flowers. The flowers are closely grouped and very full around the peduncle. The entire cluster blooms at substantially the same time. The long, full panicles on upright sturdy stems are outstanding and noticeable.

The plant has a thick stem substantially four-sided. The leaves are a dark green in color with a silvery green undersurface, lanceolate in shape and glabrous. The foliage of the plant as a whole has a clean-cut appearance, and the blossom has a slight, pleasant fragrance.

The following is a detailed description of the new variety:

*Bush*

Size: 4 to 6 feet.
Leaves: Glabrous. Heavy—normal.
*Length.*—About 4 inches.
*Quality.*—Leathery.
*Color.*—Upper surface—dark green. Under surface—artichoke green.
*Shape.*—Lanceolate.
Stems: Erect, sturdy, substantially four-sided.
*Growth.*—Heavy.
*Length.*—5 to 6 feet.
*Color.*—New, green. Old, brown.
*Texture.*—New, smooth. Old, smooth.
Branches (angle of attachment) 45°.
Twigs (angle of attachment) 45°.

*Flower*

Buds: Formed in summer.
Bloom:
*Color.*—Campanula.
*Formed.*—In panicles or clusters, very full.
Seeds:
*Size.*—¼ inch in length.
*Shape.*—Long, narrow and winged.
*Number.*—25 to 75 per pod.
*Color.*—Brown.
Ripening period: September—October.

The color designations according to "A Dictionary of Color by Maerz and Paul" are as follows:

| | Color | Plate | Letter | No. |
|---|---|---|---|---|
| Body of flower | Campanula | 42 | J | 10 |
| Tube base of single floret | | 46 | K | 5 |
| Outside ring of eye | Sunflower | 9 | L | 4 |
| Body color of eye | Burnt orange | 3 | E | 12 |
| Buds | | 18 | E | 4 |
| Main leaf color | | 24 | L | 10 |
| Back of leaf | Artichoke green. | 20 | B | 2 |
| Stem (near blossom) | Glaucous | 19 | B | 3 |
| Stem (main section) | | 21 | K | 1 |

This new variety of Buddleia is easily distinguished from other varieties by its unusual coloring and fullness of bloom.

Having thus disclosed the invention, I claim:

A new and useful variety of Buddleia plant with features in combination substantially as shown and described, characterized particularly by the unusual campanula color of its blossoms, fullness of bloom, two-toned, orange eye of each floret, stellate appearance of the panicle, well-proportioned appearance of the plant as a whole, and sturdy substantially square stems.

KARLE A. LUCAL.